(12) United States Patent
Tumbers

(10) Patent No.: US 8,568,800 B2
(45) Date of Patent: Oct. 29, 2013

(54) INSECT AND DISEASE CONTROL

(75) Inventor: Neil Tumbers, Swan Bay (AU)

(73) Assignee: Hurstwell Pty Ltd, Swan Bay, NSW (AU)

( * ) Notice: Subject to any disclaimer, the term of this patent is extended or adjusted under 35 U.S.C. 154(b) by 0 days.

(21) Appl. No.: 13/378,591

(22) PCT Filed: Jun. 15, 2010

(86) PCT No.: PCT/AU2010/000734
§ 371 (c)(1),
(2), (4) Date: Dec. 23, 2011

(87) PCT Pub. No.: WO2010/144950
PCT Pub. Date: Dec. 23, 2010

(65) Prior Publication Data
US 2012/0114769 A1    May 10, 2012

(30) Foreign Application Priority Data
Jun. 15, 2009 (AU) ................... 2009902742

(51) Int. Cl.
*A01N 65/00* (2009.01)
(52) U.S. Cl.
USPC .......................................... 424/725

(58) Field of Classification Search
None
See application file for complete search history.

(56) References Cited

U.S. PATENT DOCUMENTS

| | | |
|---|---|---|
| 6,251,440 B1 | 6/2001 | Ryan et al. |
| 6,523,496 B1 | 2/2003 | Kiethly et al. |
| 2007/0266957 A1 | 11/2007 | Tozaka et al. |

FOREIGN PATENT DOCUMENTS

WO    2006/116778 A2    11/2006

OTHER PUBLICATIONS

George et al., "The influence of 'time since last blood meal' on the toxicity of essential oils to the poultry red mite (*Dermanyssus gallinae*)", Veterinary Parasitology, 2008, pp. 333-335, 155, Elsevier B.V.
International Search Repot mailed Jul. 12, 2010.

*Primary Examiner* — Michael Meller
(74) *Attorney, Agent, or Firm* — Howard & Howard Attorneys PLLC

(57) ABSTRACT

The invention provides a method for controlling pests or pathogenic organisms in an agricultural structure, the method comprising applying a pesticidal composition to surfaces susceptible to infestation or colonization by the pest or pathogenic organism, wherein the composition includes terpenoids, essential oils, plant extracts, or combinations thereof.

1 Claim, No Drawings

INSECT AND DISEASE CONTROL

CROSS REFERENCE TO RELATED APPLICATION

This application is a national stage application of PCT Application No. PCT/AU2010/000734, filed Jun. 15, 2010, which claims priority to Australian Patent Application No. 2009/902742, filed Jun. 15, 2009, the disclosures of which are hereby incorporated by reference their entirety.

FIELD OF THE INVENTION

The present invention relates to methods for controlling pests and diseases, especially in agricultural structures, such as in grain storage structures or intensively-farmed livestock buildings, such as chicken sheds, in which pests and diseases may thrive. The present invention is particularly adapted to control of darkling beetle (or lesser mealworm beetle; *Alphitobius diaperinus*), and diseases for which it may be a vector, in chicken or poultry sheds, although it may also find application in control of pests and diseases in other agricultural structures, such as those used for rearing pigs or cattle, as well as grain storage silos, and the like.

BACKGROUND TO THE INVENTION

At least in Australia, methods for the control of insect pests in agricultural situations, including grain storage facilities and animal rearing enclosures, typically comprise the use of highly toxic chemicals, including organophosphates and carbamates, which typically require the involvement of skilled technicians for their application.

However, evidence indicates that at least certain insect pests are developing resistance to these chemicals, and some of these pests, especially certain beetle larvae, adopt behavioural mechanisms, such as burrowing, when disturbed, which reduce the effectiveness of the chemical treatments.

One particularly evident case of this is the increasing problem being posed by the darkling beetle in intensive chicken farming. The darkling beetle, *Alphitobius diaperinus* (Panzer) (or its larva, the lesser mealworm), a member of the tenebrionid family of beetles, is now a common pest of poultry houses, in particular broiler sheds and egg barns. The larvae of this beetle are often present in the litter of chicken sheds in vast numbers, reducing yield (due to consumption of the chicken feed_, and being capable of leucosis or Marek's disease, Gumboro disease, turkey coronavirus, Newcastle disease, ionfectious bursal disease, reovirus, enterovirus, fowl pox, and avian influenza; bacteria such as *Salmonella typhimurium, Campylobacter, Escherichia coli*, and *Staphylococcus* ssp.; protozoans such as *Eimeria* ssp. that cause coccidiosis; fungi such as *Aspergillus* SPP.; HELMINTHS SUCH AS THE NEMATODE *Subulura brumpti* Lopes-Neira; and fowl cestodes. There are also human-related disease risks associated with exposure to this beetle. In addition, the beetle and/or their larvae are known to damage soft materials, such as Styrofoam, fiberglass, and polystyrene insulation panels in the walls of poultry houses, especially when seeking pupation sites. The resulting damage can cause increased heating bills and additional building repair costs when the infested area is replaced.

Because of its tropical origin, the lesser mealworm is well suited for warm, humid conditions, such as frequently occur in chicken sheds. After mating, a female beetle has the potential to lay over 2,000 eggs, and does so in cracks and crevices in the poultry house or ground, in manure or litter, in grain hulls, and under feed and water lines. Adults can live three to twelve months, with females continuing to produce eggs most of their life at one to five day intervals. Larvae hatch in four to seven days and complete development to the adult stage in 40 to 100 days, depending on temperature, humidity and food quality, chicken sheds providing near, if not ideal conditions (including high humidity, temperatures between 30 and 40° C., and copious nutrients including chicken feed, chicken faeces, feathers and dead chicks).

Typically, maintenance, disinfection and disinfestation of chicken sheds in Australia is carried out in approximately 50 day cycles, with an approximately seven week growing period for the chickens. Once the market-ready chickens are removed from the sheds, the sheds are cleaned out, including the waste litter. The sheds are then washed down with an alkaline wash, inspected, and then sprayed with an organophosphate or carbamate, such as fenitrothion or carbaryl, by a licensed contractor. Formaldehyde is typically also sprayed after the insecticide treatment, as an antiviral treatment (although this is highly toxic to most organisms), and the sheds need to be left vacant for 2 to 3 days after this. Once treated, fresh litter is laid on the ground of the shed, and chickens introduced (typically over a two week period in a time-stepped procedure).

Notwithstanding the use of toxic chemicals, such as fenitrothion and cyfluthrin, often followed up by formaldehyde or glutaraldehyde treatments (requiring leaving the chicken sheds empty for up to three days), darkling beetle loads in Australian chicken sheds have been increasing rapidly, and the beetle numbers observed reflect poor kill of the larvae or adult beetles during the maintenance/disinfestation cycle.

Studies have indicated that many beetles and larvae stay concealed in the floor, and or in wall structures and/or insulation, especially when disturbed, thereby avoiding contact with toxic levels of the insecticides. This results in ever increasing starting populations of the pests in subsequent rearing cycles, and reduced yields as a result of waste litter also creates problems in terms of release of large numbers of pests into the environment, along with any diseases they carry, when the litter is disposed of.

The darkling beetle is also a pest of stored flour, meal, and other grain products, especially in poorly maintained grain processing plants or storage structures.

A number of other pests of agricultural structures exist, many of them being residual levels of pesticide in the structures and/or stored grain is of increasing concern.

There is a need for improved methods for controlling the presence and/or spread of pests or pathogenic organisms in agricultural structures which involves the use of less toxic substances. There is also a need for more effective methods for controlling the numbers and/or the spread of such pests or pathogenic organisms in said structures.

SUMMARY OF THE INVENTION

Through the present studies, it has been found that effective control of pests and pathogenic organisms in agricultural structures can be achieved without the need for organophosphates or carbamates.

Thus, according to an aspect of the invention, there is provided a method for controlling one or more pests or pathogenic organisms or a combination thereof in an agricultural structure, said method comprising applying a pesticidal composition to at least one surface(s) susceptible to infestation or colonization by said pest or pathogenic organism, wherein said composition does not comprise an organophosphate or a carbamate pesticide other than low toxicity growth regulators.

The agricultural structure may be an animal rearing enclosure, such as a shed for rearing poultry, and the pesticidal composition may be applied to at least the ground surface of the enclosure in between animal rearing cycles, after waster litter from the previous animal rearing cycle has been removed. According to an embodiment, the pesticidal composition is also applied to the walls of said enclosure.

During the present studies, it has also been found that applying a layer of an appropriate absorbent/absorbent material, such as a zeolite or analogue thereof, to the ground surface of an animal enclosure, treating the ground surface of the enclosure with a pesticidal composition before, after or both before and after applying the layer of absorbent material, or applying such an absorbent material which is pre-charged with the pesticidal composition, a barrier to pests returning into the enclosure from the ground can be achieved, providing more effective control of pest species. The use of zeolite provides the added advantage that the incidence of ammonia flushes in the animal enclosures (which can be toxic to the resident animals) can be reduced, and may also at least aide in deodorizing the enclosure and/or waste litter.

Thus, according to an embodiment of the methods of the invention, a layer of zeolite or analogue thereof is applied to the ground surface before or after the ground surface is treated with the composition. According to a further embodiment, the pesticidal composition is applied to the ground surface before said layer of zeolite or analogue thereof is applied to the ground, and to said layer of zeolite or analogue thereof. According to yet another embodiment, the zeolite or analogue thereof is pre-charged with said pesticidal composition and is applied to the ground surface of said agricultural structure. In an alternative embodiment, the step of applying the pesticidal composition to the ground surface of the agricultural structure comprises said pesticidal composition being applied to the ground surface of said structure as a layer of zeolite or analogue thereof pre-charged with said pesticidal composition.

Fresh litter is applied to the floor of an animal enclosure, on top of the treated ground surface (including layer of zeolite, or analogue thereof, if applied) before introduction of animals to the enclosure. The fresh litter may also be treated with the pesticidal composition. Alternatively, fresh litter may be introduced into the animal enclosure before applying the pesticidal composition, and the composition applied to the litter.

According to an embodiment of the methods of the present invention, the pesticidal composition is also disinfectant.

According to a particular embodiment, the pesticidal composition comprises: at least one wetting agent; one or more terpenoids, essential oils or plant extracts, or any combination thereof; and water.

According to an embodiment, the wetting agent may comprise an α-olefin sulphonated (or mixture thereof), or an alkali or alkaline earth metal salt of an alkyl sulphonic acid ester, such as sodium lauryl sulphate, sodium dodecylbenzene sulphonated or any combination thereof.

According to an embodiment, the one or more terpenoids do not comprise a pyrethroid, but may be monoterpenes. Suitable monoterpenes comprising 1,8-cineole, terpen-4-ol, terpinen-4-ol or a combination thereof. Alternatively, said one or more terpenoids may be provided in tea tree oil, eucalyptus oil, or a combination thereof.

The pesticidal composition may also comprise at least one $C_1$ or $C_5$ alcohol. One exemplary alcohol for inclusion in compositions for use in methods according to the invention, is ethanol.

According to one embodiment of the methods of the invention, the pesticidal composition is applied at a rate sufficient to deliver to each $m^2$ of at least the ground surface of the agricultural structure:

(a) from about 1 g to about 20 g of at least one wetting agent; and (b) from about 0.1 g to about 10 g of at least one terpenoid.

According to another embodiment, the pesticidal composition is applied at a rate sufficient to deliver to each $m^2$ of at least the ground surface of the agricultural structure:

(a) from about 1 g to about 20 b of at least one wetting agent;

(b) from about 2 mL to about 40 mL of at least one $C_1$ to $C_5$ alcohol; and (c) from about 0.1 g to about 10 g of at least one terpenoid.

According to another embodiment, the pesticidal composition is applied at a rate sufficient to deliver to each $m^2$ of at least the ground surface of the agricultural structure:

(a) from about 1 g to about 20 g of at least one wetting agent;

(b) from about 2 mL to about 40 mL of at least one $C_1$ to $C_5$ alcohol;

(c) from about 0.1 g to about 10 g of at least one terpenoid; and (d) from about 0.1 to about 10 g of at least one nitrogenous agent.

According to another embodiment, the pesticidal composition is applied at a rate sufficient to deliver to each $m^2$ of at least the ground surface of the agricultural structure:

(a) from about 1 g to about 20 g of at least one wetting agent selected from α-olefin sulphonates, an alkali or alkaline earth metal salt of an alkyl or aralkyl sulphonic acid ester, or any combination thereof;

(b) from about 0.05 g to about 1 g of coconut diethylamide;

(c) from about 15 mL to about 30 mL of ethanol;

(d) from about 0.25 g to about 5 g of a mixture of tea tree and eucalyptus oils; and (e) from about 0.5 to about 5 g of urea.

The one or more pests to be controlled by the methods of the invention may be insects, and may be beetles or larvae thereof, and may be a member of the Anobiidae, Anthribidae, Bostrichidae, Chrysomelidae, Curculionidae, Dermestidae, Laemophloeidae, Nitidulidae, Scarabaeidae, or Tenebrionidae. According to an embodiment, the beetle is a member of the Tenebrionidae, and may be of the genus *Alphitobius, Gnathocerus, Latheticus, Omophlus, Tenebrio*, or *Tribolium*. According to a specific embodiment of the methods of the present invention, the pest is of the species *Alphitobius diaperinus*.

The one or more pathogenic organisms to be controlled by methods of the present invention may be selected from viruses, bacteria, fungi, protozoans, helminthes or cestodes. Viruses which are particularly important to control in poultry sheds include virus associated with leucosis or Marek's disease, Gumboro disease, turkey coronavirus, Newcastle disease, infectious bursal disease, reovirus, enterovirus, fowl pox, or avian influenza. Bacteria which are particularly important to control in poultry sheds include bacteria of the genus *Salmonella, Camphlobacter, Escherichia*, or *Staphylococcus*. Fungi Aspergillus. Protozoans of the genus *Eimeria* associated with coccidiosis are also contemplated as targets for control by methods of the present invention.

According to a specific embodiment, a method of the present invention is a method for maintenance, disinfestation or maintenance and disinfestation method for controlling at least a pest insect species in intensively farmed animal enclosures, and in an embodiment may comprise:

applying a pesticidal composition as described above to at least the ground surface of said enclosure, wherein said composition does not comprise an organophosphate or a carbamate pesticide;

applying a layer of zeolite or analogue thereof to the treated ground surface and applying a layer of litter material to the ground surface of said enclosure.

According to an embodiment, the enclosure comprises a shed for rearing poultry and, in a further embodiment, maintenance, disinfestation or maintenance and disinfestation is for controlling a beetle of the species *Alphitobius diaperinus* and any pathogenic organisms associated herewith.

The composition may advantageously also be applied to the walls of said enclosure and/or to the zeolite or analogue thereof. The zeolite or analogue thereof may be pre-charged with said pesticidal composition.

During the present studies, it has also been found that the waste littler comprising zeolite or an analogue thereof from an animal enclosure can be processed into a fertilizer with a least partial slow or delayed nutrient release properties.

Thus, according to another embodiment, a method of the invention may comprise animals being introduced into the enclosure after the enclosure has been treated with the pesticidal composition and zeolite or analogue thereof and fresh littler laid down, reared and then harvested, and the resulting waste material comprising litter, animal waste and zeolite or analogue thereof being processed into a fertilizer.

Thus, the present invention also provides waste litter recovered from animal enclosures treated by methods of the present invention, after animals have been reared in those enclosures and then harvested. The present invention also provides a fertilizer product manufactured from that waste or, alternatively, a soil improvement product manufactured from that waste.

The present invention also provides a zeolite or analogue thereof for use in a method of the invention, and which is charged with a pesticidal composition as described above.

DETAILED DESCRIPTION OF THE INVENTION

Definitions

As used herein, the term "about", is relative to the actual value stated, as will be appreciated by those of skill in the art, and may encompass, for example, the stated value +/− approximately 50% of the stated value.

As used herein, the term "animal" encompasses all domestic animals, including especially, but no exclusively, mammals and birds, with particular focus on agriculturally relevant animals (livestock), such as poultry, cattle, pigs, horses, llamas, alpacas, sheep, goats, although encaged/zoological animal specimens, including enclosed domestic animals (such as may be raised in aviaries, terrariums and the like) are also intended to be included within the scope of this term.

As used herein, the term "comprising" means "including principally, but not necessarily solely". Variations of the word "comprising", such as "comprise" and "comprises", have correspondingly similar meanings.

"Controlling", as referred to herein, refers to any and all uses which remedy or prevent a disease or infestation in an agricultural structure, or otherwise prevent, hinder, retard, or reverse the progression of infestation/disease in any way whatsoever, including indirect means, such as preventing, controlling or reversing infestation of an agricultural structure by vectors for a pathogenic organism.

The term "wherein said composition does not comprise an organophosphate or a carbamate pesticide" as used herein is intended to mean that a composition does not comprise amounts of an organophosphate or carbamate pesticide which are toxic to animals (including humans), but which may comprise small or non-significant amounts of an organophosphate or carbamate pesticide.

The term "poultry" as used herein refers to any bird raised commercial for meat or other products (including eggs or feathers), and includes, without being limited to, chickens, ducks, turkeys, geese, quails, and pheasants.

As used herein, the term "terpenoids" relates to any of numerous unsaturated hydrocarbons $(C_5H_8)_n$ derived wholly or partly from isoprene units ($—CH_2—C(CH_3)=CH—CH_2—$) joined head to tail, tail to head, head to head or tail to tail. Terpenoids, as used herein include terpenes and derivatives thereof which may be aliphatic, alicyclic, mono-, di-, tri- or polycyclic. Terpenoids include compounds commonly found in plant extracts, essential oils, resins, and balsams, and include natural and synthetic monoterpenes ($C_{10}H_{16}$), sesquiterpenes ($C_{15}H_{24}$), diterpenes ($C_{20}H_{32}$) and higher isoprene polymers, as well as derivatives thereof, including saturated, unsaturated, aromatic, oxidized and/or reduced derivatives.

As used herein, the term "wetting agent" refers to any agent which will act as a surfactant to reduce surface tension of the components of the composition such that the various components of the composition, some of which are immiscible, will be able to mix to form a homogenous solution. A wetting agent will also facilitate even spreading of the compositions of the present invention over a surface that displays hydrophobic properties, such as an insect and/or soil surface. Advantageously, a wetting agent may also aid in breaking down, or permeating a hydrophobic barrier, such as an insect surface.

As used herein, the term "zeolite or analogue there" refers to materials which, due to their ion exchanged capacity, microporous nature or ion exchange capacity and microporous nature are able to sequester certain molecular species from an environment. Of particular interest to the present invention is the ability of the material to sequester ammonium, ammonia or both from litter in chicken sheds. Also important, although not necessarily essential to the present invention is the capacity of the material to retain an effective amount of a pesticidal composition. Zeolites are ideally suited to these tasks, due to their high cation exchange capacity and microporous structure. It will be appreciated, however, that other materials such as clays, clay-like minerals, expandable clays, ion0exchange resins, ferrous sulphate impregnated ceramics, chabazite, carbon (such as activated charcoal), or any other material which act as an ion exchange medium with ammonium can also be used in connection with the present invention.

Methods for Controlling Pests or Pathogenic Organisms

The present invention relates to safer methods for treating/controlling pest and/or disease infestation of agricultural structures. The present invention also relates to more effective means for treating/controlling pest and/or disease infestation of agricultural structures.

Current methods for treating or controlling disease and pest infestation of agricultural structures, including poultry sheds, employ chemicals which are not only highly deadly to the pest and/or disease, but which are also highly toxic to animals, including humans, and which may have residual effects. The current methods are also becoming inefficient due to increased resistance of the pest and/or diseases due to increasing resistance to the treatment(s) and, in some cases, behavioural traits of target pets, including burrowing into soil and/or wall materials such as insulation).

Through the present studies, it has been found that effective control of pests and pathogenic organisms in agricultural structures can be achieved without the need for organophosphates or carbamates of high toxicity to animals (including humans). The present invention accordingly provides a method for controlling one or more pests or pathogenic organisms or a combination thereof in an agricultural structure, said method comprising applying a pesticidal composition to at least one surface(s) susceptible to infestation or colonization by said pest or pathogenic organism, wherein said composition does not comprise an organophosphate or a carbamate pesticide other than low toxicity growth regulators (for example, fenoxycarb).

Although the methods of the present invention may be employed for the treatment of any relevant agricultural structure, treatment of storage structures and animal rearing enclosures, including poultry sheds and piggery sheds, is particularly contemplated, and the methods of the present invention find particular application in poultry sheds, in which pests such as the darkling beetle (*Alphitobius diaperinus*; lesser mealworm) are becoming very significant due to their apparent increased resistance to current treatments, the economic effect they have through reduced yield (by competing with chicks for food) and damage to the sheds (especially insulation). Darkling beetles and larvae burrow into the soil or other surfaces of animal enclosures where disturbed, such as when animal enclosures are cleared out and during servicing of enclosures between animal rearing cycles. When fresh litter is placed into the animal enclosures, the feed reintroduced, the beetles and/or larvae surviving from the servicing treatment exit from their burrowing sites and proceed to multiply and compete for food with the animals. Treatment of grain storage structures is also contemplated for similar reasons (although there is no competition with livestock for feed).

The pesticidal composition may be applied to at least the ground surface of agricultural structures in between animal rearing cycles, after waster litter from the previous animal rearing cycle has been removed. Advantageously, the pesticidal composition is also applied to the walls of the structure, to control pests burrowed in soft materials in the walls as well as washing them down, replacing current alkaline wash procedures. Compositions and rates and modes of application are described further below.

The present studies have also found that forming a barrier to the pests is effective in controlling pests numbers, most likely through reducing the incidence of pests returning from burrowing sites in the soil Such a barrier may be achieved by applying a layer of an appropriate absorbent/absorbent material, such as a zeolite or analogue thereof, to the ground surface of an animal enclosure, treating the ground surface of the enclosure with a pesticidal composition before, after or both before and after applying the layer of absorbent material (that is, a method of the invention could be carried out by spraying the pesticidal solution on the layer of zeolite or analogue thereof which, once laid, becomes the ground surface). Alternatively, a method of the invention could comprise applying to the ground surface of the animal enclosure a layer of zeolite or analogue thereof which is pre-charged with the pesticidal composition. Such a pre-charged layer of zeolite or analogue thereof may comprise the treatment of the ground surface with the composition, or the ground surface may be treated with the pesticidal composition before the layer of pre-charged zeolite or analogue thereof is applied.

The use of zeolite provides the added advantage that the incidence of ammonia flushes in the animal enclosures, which are commonplace in, for example, poultry sheds, and can lead to significant chick death, can be reduced.

Zeolites are typically aluminosilicates which may be naturally occurring volcanic minerals or synthesized materials and have a three-dimensional interconnecting lattice structure. Zeolites have the ability to selectively absorb/absorb and desorb specific molecules. One particular form of zeolite, clinoptilolite is known to have high selectivity for ammonium ions, and is therefore a preferred form of zeolite for use in methods of the invention. However, other zeolites, including synthetic zeolites may be used, as well as any suitable analogue. Such analogues include, but are not intended to be restricted to clays, clay-like minerals, expandable clays, ion-exchange resins, ferrous sulphate impregnated ceramics, chabazite, carbon (such as activated charcoal), or any other material which can act as an ion exchanged medium with ammonium. As an additional advantage, zeolites such as clinoptilolite are typically non-toxic, edible and easily digested and have been used as food supplement for livestock to improve metabolism and lessen bloating. As such, it is safe and does not pose the health problems associated with other sequesters such as lime. Ammonium ions are absorbed by the clinoptilolite, reducing the incidence of airborne ammonia typically found in areas where animals are housed. The reduction of airborne ammonia reduces respiratory distress and mortality of, especially, chicks, which it is known to cause.

Zeolites, and in particular clinoptilolite, also have excellent agricultural fertilization properties. This allows for economical, or even profitable disposal of the waste litter, which can be processed into a fertilizer product with at least partially slow release properties—clinoptilolite is high in potassium as a major exchangeable cation, providing slow potassium, and nitrogen when loaded with ammonium from animal excreta.

Alternatively, the waste litter can be processed into a soil improvement or remediation agent. Many soils have poor moisture and nutrient retention characteristics, and many others may be acidified either through natural or, more typically, artificial circumstances, including extended use of fertilizers, especially super phosphate, or exposure of certain previously water-logged soils to oxidative conditions resulting in acid sulphate soils, which have a pH below 3, and which therefore will only allow for growth of certain plant species, if any. The large cation exchanging capacity of the zeolites or analogues thereof, ammonium sequestered thereto, and porosity may allow for increased nutrient retention (and/or controlled release thereof), increased water retention, pH adjustment and/or buffering. Thus, a soil improvement/remediation product produced from waste litter recovered from an agricultural structure treated by a method of the present invention (and in which animals have then been reared) may be used to improve such soils.

An additional advantage of using zeolites or analogues thereof is the resulting reduction in noxious odours, which can be a source of complaints from neighbours adjoining an animal production facility.

The zeolite or analogue thereof ma be milled to an average particle size of form about 25 μm to about 10 mm, such as from about 25 μm to about 8 mm, from about 25 μm to about 6 mm, from about 25 μm to about 4 mm, from about 25 μm to about 2 mm, from about 25 μm to about 1 mm, from about 25 μm to about 800 μm, from about 25 μm to about 600 μm, from about 25 μm to about 500 μm, from about 25 μm to about 400 μm, from about 25 μm to about 300 μm, from about 25 μm to about 200 µm, from about 25 µm to about 150 µm, from about 25 µm to about 100 µm, from about 25 µm to about 50 µm, from about 50 µm to about 8 mm, from about 75 µm to about 8 mm, from about 100 µm to about 8 mm, from about 150 µm to about 8 mm, from about 200 µm to about 8 mm, from about 300 µm to about 8 mm, from about 400 µm to about 8 mm, from about 500 µm to about 8 mm, from about 600 µm to about 8 mm, from about 800 µm to about 8 mm, from about 1 mm to about 8 mm, from about 2 mm to about 8 mm, from about 4 mm to about 8 mm, from about 6 mm to about 8 mm, about 50 µm, about 75 µm, about 100 µm, about 150 µm, about 200 µm, about 250 µm, about 300 µm, about 350 µm, about 400 µm, about 450 µm, about 500 µm, about 600 µm, about 700 µm, about 800 µm, about 900 µm, about 1 mm, about 1.5 mm, about 2 mm, about 2.5 mm, about 3 mm, about 3.5 mm, about 4 mm, or an average particle size in a range comprising any combination of the aforementioned particle sized and upper and lower limits thereof.

Zeolite or an analogue thereof may be applied to the ground surface of the agricultural structure at any appropriate rate, which however may depend on the characteristics of the material, including cation exchange capacity, absorptive capacity and cost. However, as a guide, not intended to be limiting, zeolite or an analogue thereof may be applied to the ground surface of an agricultural structure at a rate of from about 50 g/m$^2$ up to a rate of about 10 kg/m$^2$, such as from about 100 g/m$^2$ up to about 8 kg/m$^2$, from about 150 g/m$^2$ up to about 6 kg/m$^2$, from about 150 g/m$^2$ up to about 4 kg/m$^2$, from about 300 g/m$^2$ up to about 4 kg/m$^2$, from about 500 g/m$^2$ up to about 3.5 kg/m$^2$, from about 700 g/m$^2$ up to about 3 kg/m$^2$, from about 800 g/m$^2$ up to about 2.5 kg/m$^2$, from about 900 g/m$^2$ up to about 2 kg/m$^2$, from about 1 kg/m$^2$ up to about 1.5 kg/m$^2$, about 150 g/m$^2$, about 300 g/m$^2$, about 500 g/m$^2$, about 700 g/m$^2$2, about 900 g/m$^2$, about 1 kg/m$^2$, about 1.5 kg/m$^2$, about 2 kg/m$^2$, about 2.5 kg/m$^2$, about 3 kg/m$^2$, about 4 kg/m$^2$, or at a rate in a range comprising any combination of the aforementioned rates and upper and lower limited thereof.

After treatment of an agricultural structure with pesticidal composition (and optionally a zeolite or analogue thereof) fresh litter is applied to the floor of the structure, on top of the treated ground surface (including layer of zeolite, or analogue thereof, if applied) before introduction of animals to the enclosure.

As an alternative to using zeolite to produce a barrier, the fresh litter may be placed in the agricultural structure either before or after treatment of the ground surface of applied to the litter material, as the composition is not toxic to the animals.

Suitable litter material may comprise any suitably absorptive or adsorptive material known for use as bedding/litter material for animal housing, including sawdust, wood shavings, herbaceous or ligneous mulch, or a combination thereof, shredded cardboard or paper (such as waste paper), recycled fibrous materials in granulated form, waste fibrous and/or ligneous materials resulting from wood or plant processing or cultivation, or even synthetic materials (including recycled materials) which appropriate absorptive properties.

Fresh litter material may be laid on the ground surface (whether previously overlaid with zeolite or analogue thereof or not) at any suitable rate as already known to those involved with running of animal rearing enclosures, which will depend on the amount of time period over which the litter material is to be used, as well as the absorptive/adsorptive properties of the material. However, as a non-limiting approximate guide, fresh litter material may be introduced into an animal enclosure at a rate of from about 1 Liter/m$^2$ to about 50 Liters/m$^2$, such as from about 2 L/m$^2$ to about 40 L/m$^2$, from about 3 L/m$^2$ to about 30 L/m$^2$, from about 3 L/m$^2$ to about 20 L/m$^2$, from about 3 L/m$^2$ to about 15 L/m$^2$, from about 3 L/m$^2$ to about 10 L/m$^2$, from about 3 L/m$^2$ to about 8 L/m$^2$, from about 3 L/m$^2$ to about 6 L/m$^2$, from about 3 L/m$^2$ to about 4 L/m$^2$, from about 4 L/m$^2$ to about 20 L/m$^2$, from about 6 L/m$^2$ to about 20 L/m$^2$, from about 8 L/m$^2$ to about 20 L/m$^2$, from about 10 L/m$^2$ to about 20 L/m$^2$, from about 10 L/m$^2$ to about 15 L/m$^2$, about 4 L/m$^2$, about 6 L/m$^2$, about 8 L/m$^2$, about 10 L/m$^2$, about 12 L/m$^2$, about 14 L/m$^2$, about 16 L/m$^2$, about 18 L/m$^2$, about 20 L/m$^2$, or at a rate in a range comprising any combination of the aforementioned rates and upper and lower limits thereof.

Pesticidal Compositions

Pesticidal compositions fur use in the methods of the present invention may include any suitable pesticidal composition, provided it does not comprise an animal-toxic organophosphate or carbamate pesticide, such pesticides being neurotoxins highly toxic to mammals, birds and other organisms, and which are often persistent, at least to some degree, in the environment. Organophosphate and carbamate pesticides can often also only be applied by a licensed specialist.

According to an embodiment, the pesticidal composition is also disinfectant. According to an embodiment the pesticidal compositions for use in methods of the present invention comprise at least one wetting agent, one or more agents selected from terpenoids, plant essential oils or plant extracts, and water.

According to a further embodiment the pesticidal compositions for use in methods of the present invention comprise at least one wetting agent, one or more terpenoids and water. Said terpenoids may also be replaced, either completely or partially by one or more growth/development inhibitors or regulators, such as juvenile hormones, anti-juvenile hormones or analogues or derivatives thereof, and which may be selected from, for example, juvenile hormone (which is a terpenoid), diflubenzuron, hexaflumuron, teflubenzuron, flufenoxuron, fenoxycarb (which, although a carbamate, has only limited toxicity to mammals and birds and does not require a licensed technician for application), tebufenozide, methoxyfenozide, cyromazine, epofenonane, kinoprene, methoprene, triprene, hydroprene, pyriproxyfen, or allatostatins (such as allatostatins 1, 2, 3 or 4).

The wetting agent may comprise any suitable substance which will act as a surfactant to reduce surface tension of the components of the composition such that the various components of the composition, some of which are immiscible, will be able to mix to form a homogenous solution. The wetting agent may also facilitate even spreading of the compositions of the present invention over a surface that displays hydrophobic properties, such as an insect surface. Advantageously, a wetting agent may also aid in breaking down, or permeating a hydrophobic barrier, such as an insect surface.

Examples of suitable wetting agents for inclusion in compositions for use in methods of the present invention include ionic or nonionic surfactants or a mixture thereof. Among those surfactants which may be used, for example, are polyacrylic acid salts, lignosulphonic acid salts, the condensation of fatty acids or aliphatic amines or amides containing at least 12 carbon atoms in the molecule with ethylene oxide and/or propylene oxide; fatty acid esters of glycerol, sorbitol, sorbitan, sucrose, or pentaerythritol; condensates of these with ethylene oxide and/or propylene oxide; condensates of these with ethylene oxide and/or propylene oxide; condensation products of fatty alcohol or alkyl phenols, for example p-octylphenol or p-octylcresol, with ethylene oxide and/or propylene oxide; suphates or sulphonates of these condensation products; α0olefin sulphonates; alkali or alkaline earth metal salts of fatty acids, preferably sodium salts, or sulphuric or sulphonic acid esters thereof containing at least 10 carbon atoms in the molecule, for example sodium lauryl sulphate, sodium secondary alkyl sulphates, sodium salts of sulphonated castor oil, and sodium alkylaryl (aralkyl) sulphonates such as sodium dodecylbenzene sulphonated; and polymers of ethylene oxide and copolymers of ethylene oxide and propylene oxide, phenolsulphonic or naphthalenesulphonic acid salts, polycondensates of ethylene oxide with fatty alcohols or fatty acids or fatty esters or fatty amines, substituted phenols (in particular alkylphenols or arylphenols), estersalts of sulphosuccinic acid, taurine derivatives (in particular alkyl taurates), phosphoric esters of alcohols or of polycondensates of ethylene oxide with phenols, fatty acid esters with polyols, or sulphate, sulphonated or phosphate functional derivates of the compound described above. According to an embodiment the wetting agent comprises an α-olefin sulphonated (or mixture there), or an alkali or alkaline earth metal salt of an alkyl or alkylaryl sulphuric or sulphonic acid ester, such as sodium lauryl sulphate, sodium dodecylbenzenesulphonate or any mixture thereof. According to a further embodiment, the composition may comprise an α-olefin sulphonated (or mixture thereof), or an alkali or alkaline earth metal salt of an alkyl or aralkyl sulphonic acid ester, such as sodium lauryl sulphonated or sodium dodecylbenzene sulphonated, or any mixture thereof and coconut diethylamide.

The non-water components of the pesticidal composition may comprise from about 1% w/v to about 70% w/v of a wetting agent, such as from about 1% w/v to about 65% w/v, from about 1% w/v to about 60% w/v, from about 1% w/v to about 55% w/v, from about 1% w/v to about 50% w/v, from about 1% w/v to about 45% w/v, from about 1% w/v to about 40% w/v, from about 1% w/v to about 35% w/v, from about 1% w/v to about 30% w/v, from about 1% w/v to about 25% w/v, from about 1% w/v to about 20% w/v, from about 1% w/v to about 15% w/v, from about 1% w/v to about 10% w/v, from about 1% w/v to about 5% w/v, from about 5% w/v to about 50% w/v, from about 10% w/v to about 50% w/v, from about 15% w/v to about 50% w/v, from about 20% w/v to about 50% w/v, from about 25% w/v to about 50% w/v, from about 30% w/v to about 50% w/v, from about 40% w/v to about 50% w/v, about 5% w/vm, about 10% w/v, about 15% w/v, about 20% w/v, about 25% w/v, about 30% w/v, about 35% w/v, about 40% w/v, about 45% w/v, about 50% w/v, or a wetting agent concentration in a range comprising any combination of the aforementioned concentrations and upper and lower limits thereof.

According to one embodiment of the invention, the non-water components of the pesticidal composition comprise from about 15% w/v to about 30% w/v α-olefin sulphonate (or mixture thereof), or an alkali or alkaline earth metal salt of an alkyl or aralkyl sulphuric or sulphonic acid ester, such as sodium lauryl sulphonated or sodium dodecylbenzene sulphonated, or any mixture thereof. In one specific embodiment, the non-water components of the pesticidal composition comprises about 25% w/v α-olefin sulphonated (or mixture thereof), or an alkali or alkaline earth metal salt of an alkyl or aralkyl sulphuric or sulphonic acid ester, such as sodium lauryl sulphate or sodium dodecylbenzene sulphonated, or any mixture thereof. If present as a foaming agent, coconut diethylamide may be present at a concentration of from about 0.5% w/v to about 5% w/v, such as about 0.5% w/v to about 4.5% w/v of the non-water components of the pesticidal composition, such as from about 0.5% w/v to about 4% w/v, from about 0.5% w/v to about 3.5% w/v, from about 0.5% w/v to about 3% w/v, from about 0.5% w/v to about 2.5% w/v, from about 0.5% w/v to about 2% w/v, from about 0.5% w/v to about 1.5% w/v, from about 0.5% w/v to about 1% w/v, from about 1% w/v to about 4% w/v, from about 1.5% w/v to about 4% w/v, from about 2% w/v to about 4% w/v, from about 2.5% w/v to about 4% w/v, from about 4% w/v to about 4% w/v, from about 3.5% w/v to about 4% w/v, about 0.5% w/v, about 1% w/v, about 1.5% w/v, about 2% w/v, about 2.5% w/v, about 3% w/v, about 3.5% w/v, about 4% w/v, about 4.5% w/v, or about 5% w/v, or at a concentration in a range comprising any combination of the aforementioned concentrations and upper and lower limits thereof.

The wetting agent, or one of the wetting agents may also act as a foaming agent, which may be desirable for compositions for treating walls. The alkali or alkaline earth salts of alkyl or aralkyl sulphates or sulphonates, or coconut diethylamide, or any combination thereof are convenient and effective foaming agents.

According to an embodiment, the one or more terpenoids do not comprise a pyrethroid, but may be selected from low molecular weight terpenoids, such as monoterpenes ($C_{10}$), sesquiterpenes ($C_{15}$), diterpenes ($C_{20}$), sesterterpenes ($C_{25}$), triterpenes ($C_{30}$), or derivatives thereof. Derivatives may include, for example, ketone, aldehyde, alcohol, ether, oxidized, partially reduced or fully saturated derivates. According to an embodiment the at least one terpenoid compound is a monoterpene or a derivative thereof.

Examples of suitable monoterpenes and derivatives include borneol, camphor, camphoric acid, 2-carene, 3-carene, camphene, camphor, carvone, 1,4-cineole, 1,8-cineole, cis-p-menthane, cis-pinane, p-cymene, citronellal, β-citronellen, β-citronellol, 3,7-dimethyl-1-octanol, D-limonene, dipentene, eucalyptol, α-fenchol, fenchone, geraniol, geranial, hydroxycitronellal, α-ionone, β-ionone, iso-borneol, iso-menthol, iso-pinocampheol, iso-pulegol, linalool, limonene oxide, p-menth-1-ene, menthol, menthone, β-myrcene, neomenthol, nerol, α-phellandrene, β-phellandrene, α-pinene, α-pinene oxide, β-pinene, sabinene, terpen-4-ol, terpin, α-terpinene-γ-terpinene, α-terpineol, -βterpineol, terpinen-4-ol, terpinolene, α+β-thujone, trans-isolimonene, trans-myrtanol, trans-pinane, tricyclene and sylvestrene, among many others.

Examples of sesquiterpenes and derivatives include aromadendrene, bergamotene, δ-cadinene, cedral, cedrene, cedrol, cedrenol, curcurmene, farnesal, farnesol, germacrene, globulol, guaiyl acetate, juvabione, juvenile hormone, nerolidol, laurene, longifolene, thujopsene, viridiflorol, amongst many others.

According to another embodiment the terpenoid compound(s) may comprise 1,8-cineole, terpinen-4-ol or a combination thereof. Alternatively, said one or more terpenoids may be provided in tea tree (*Melaleuca altemifolia*) oil, eucalyptus oil (which may comprise blue mallee (*Eucalyptus polybractea*) oil, which contains very high levels of 1,8-cineole, such as form about 80% w/v up to 99% w/v 1,8-cineole), or a combination thereof.

Of course a large number of plants or parts thereof produce one or more terpenoids/essential oils, in combination with other components, which may be used in the formulation of compositions for use in the methods of the present invention. Non-limiting examples of plans from which essential oils for use in the methods of the present invention can be obtained include the following:

| Botanical Name | Common Name |
| --- | --- |
| *Andropogon muricatus* | Vetiver |
| *Aniba rosaeodora* | Rosewood |
| *Azadirachta indica* | Neem |
| *Backhousia Citriodora* | Lemon Scented Myrtle |
| *Boswellia carteri* | Frankincense |
| *Cananga odorata* var. *genuine* | Ylang ylang |
| *Citrus aurantium* dulce | Sweet orange |
| *Citrus aurantium* | Bitter orange |
| *Citrus bergamia* | Bergamot |
| *Citrus limonum* | Lemon |
| *Citrus aurantifolia/latifolia* | Lime |
| *Citrus nobilis/deliciosa* | Mandarin |
| *Citrus reticulate* | Tangerine |
| *Citrus paradise* | Grapefruit |
| *Cymbopogon citratus* | Lemongrass |
| *Cymbopogon martini* | Rosh grass |
| *Eucalyptus polybractea* | Blue Mallee |
| *Eucalyptus radiate* | Narrow leaved peppermint |
| *Eucalyptus radiate* var. *australiana* | Narrow leaved peppermint |
| *Eucalyptus dives* | Broad leaved peppermint |
| *Eucalyptus globulus* | Blue Gum (also Tasmania, or Southern Blue Gum) |
| *Eucalyptus citriodora* | Lemon scented gum |
| *Ferula galbaniflua* | Galbanum |
| *Foeniculum vulgare* v. *dulce* | Sweet fennel |
| *Guaiacum officinale* | Guajacum/Guaiac/Lignum vitae |
| *Helichrysum italicum* | Everlast/immortelle |
| *Hierochloe alpine* | Alpine sweet grass |
| *Jasminum officinale* | Jasmine |
| *Juniperus communis* | Juniper |
| *Lavandula hybrida* | Lavandin |
| *Lavandula officinalis/angustifolia* | Lavender |
| *Litsea cubeba* | Litsea |
| *Melaleuca alternifolia* | Narrow leaved Tea tree |
| *Mentha piperita officinalis* | Peppermint |
| *Mentha spicata* | Spearmint |
| *Pelargonium roseum* | Geranium |
| *Petroselinum crispum* | Parsley |
| *Pinus sylvestris* | Pine |
| *Piper nigrum* | Black pepper |
| *Pogostermon patchouli* | Patchouli |
| *Polyanthes tuberose* | Tuberose |
| *Rosa damascene* | Damask Rose |
| *Rosmarinus officinalis* | Rosemary |
| *Salvia officinalis* | Sage |
| *Santalum album* | Sandalwood |
| *Tagetes patula* | Marigold |
| *Pistacia terebinthus* | Terebinth |
| *Thymus vulgaris* | Thyme |
| *Viola odorata* | Sweet violet |
| *Zingiber officinal* | Ginger |

The non-water components of the pesticidal composition may comprise from about 0.5% w/v to about 50% w/v of said one or more terpenoids, plant essential oils or plant extracts such as from about 1% w/v to about 45% w/v, from about 1% w/v to about 40% w/v, from about 1% w/v to about 35% w/v, from about 1% w/v to about 30% w/v, from about 1% w/v to about 25% w/v, from about 1% w/v to about 20% w/v, from about 1% w/v to about 15% w/v, from about 1% w/v to about 10% w/v, from about 1% w/v to about 5% w/v, from about 1.5% w/v to about 40% w/v, from about 2% w/v to about 40% w/v, from about 2.5% w/v to about 40% w/v, from about 3% w/v to about 40% w/v, from about 4% w/v to about 40% w/v, from about 5% w/v to about 40% w/v, from about 6% w/v to about 40% w/v, from about 7% w/v to about 40% w/v, from about 8% w/v to about 40% w/v, from about 9% w/v to about 40% w/v, from about 10% w/v to about 40% w/v, about 2% w/v, about 40% w/v, about 6% w/v, about 8% w/v, about 10% w/v, about 12% w/v, about 14% w/v, about 16% w/v, about 18% w/v, about 20% w/v, or a terpenoid concentration in a range comprising any combination of the aforementioned concentrations and upper and lower limits thereof.

According to one embodiment of the invention, the non-water components of the pesticidal composition comprise from about 1% w/v to about 7% w/v tea tree oil, from about 1% w/v to about 7% w/v of eucalyptus oil, or from about 2% w/v to about 14% w/v of a combination of tea tree and eucalyptus oils. In one specific embodiment, the non-water components of the pesticidal composition comprises about 3% w/v of tea tree oil and about 2% w/v of eucalyptus oil.

According to an embodiment, the pesticidal composition also comprises at least one $C_1$ to $C_{10}$ alcohol, which may be branched or linear, saturated or unsaturated, aliphatic, aromatic, alicyclic or a polyol, or any combination thereof. According to an embodiment, the at least one alcohol is a linear, branched or cyclic, saturated or unsaturated $C_1$ to $C_5$ alcohol, which may be a polyol, or any combination thereof. One exemplary alcohol for inclusion in compositions for use in methods according to the invention, is ethanol. Other alcohols which may be considered for use in compositions of the present invention may comprise methanol, propanol, isopropanol, butanol, isobutanol, tert-butylalcohol, pentanol (amyl alcohol), isoamyl alcohol, neopentyl alcohol, tent-amyl alcohol, as well as hexanol, heptanol, octanol, nonanol, decanol, cyclopentanol, cyclohexanol, cycloheptanol, benzyl alcohol, ethylene glycol, methylcyclohexanol, cyclohexyl methanol, propenol, propynol, butenol, butynol, and any isomers, including stereoisomers, regioisomers and optical isomers thereof.

The non-water components of the pesticidal composition may comprise from about 5% v/v to about 80% v/v of said alcohol, such as from about 5% v/v to about 70% v/v, from about 5% v/v to about 65% v/v, from about 5% v/v to about 60% v/v, from about 5% v/v to about 55% v/v, from about 5% v/v to about 50% v/v, from about 5% v/v to about 45% v/v, from about 5% v/v to about 40% v/v, from about 5%/v to about 35% v/v, from about 5% v/v to about 30% v/v, from about 5% v/v to about 25% v/v, from about 5% v/v to about 20% v/v, from about 5% v/v to about 15% v/v, from about 5% v/v to about 10% v/v, from about 10% v/v to about 70% v/v, from about 15% v/v to about 70% v/v, from about 20% v/v to about 70% v/v, from about 25% v/v to about 70% v/v, from about 30% v/v to about 70% v/v, from about 25% v/v to about 70% v/v, from about 40% v/v to about 70% v/v, from about 45% v/v to about 70% v/v, from about 50% v/v to about 70% v/v, from about 55% v/v to about 70% v/v, from about 60% v/v to about 70% v/v, from about 65% v/v to about 70% v/v, about 30% v/v, about 40% v/v, about 50% v/v, about 55% v/v, about 60% v/v, about 65% v/v, about 70% v/v, about 75% v/v, about 80% v/v, or an ethanol concentration in a range comprising any combination of the aforementioned concentrations and upper and lower limits thereof.

According to one embodiment of the invention, the non-water components of the pesticidal composition comprise from about 40% v/v to about 70% v/v ethanol. In one specific embodiment, the non-water components of the pesticidal composition comprise about 60% v/v of ethanol.

According to another embodiment, the pesticidal composition may comprise at least one nitrogenous agent. According to an embodiment, the at least one nitrogenous agent comprises a small organic or inorganic molecule comprising between one and five nitrogen atoms which may comprise amines, amides, azides, imines, imides, nitriles, nitroso compounds, nitrates, nitrites, ammonium ions, or any combination thereof. According to an embodiment, the at least one nitrogenous agent comprises urea. The at least one nitrogenous agent may comprise from about 2% w/v to about 10% w/v of the non-water components of the pesticidal composition, such as from about 2% w/v to about 10% w/v, from about 2% w/v to about 9% w/v, from about 2% w/v to about 8% w/v, from about 2% w/v to about 7% w/v, from about 2% w/v to about 6% w/v, from about 2% w/v to about 5% w/v, from about 2% w/v to about 4% w/v, from about 2% w/v to about 3% w/v, from about 3% w/v to about 10% w/v, from about 4% w/v to about 10% w/v, from about 5% w/v to about 10% w/v, from about 6% w/v to about 10% w/v, from about 7% w/v to about 10% w/v, from about 8% w/v to about 10% w/v, from about 9% w/v to about 10% w/v, about 2% w/v, About 3% w/v, about 4% w/v, about 5% w/v, about 6% w/v, about 7% w/v, about 8% w/v, about 9% w/v, about 10% w/v, or a nitrogenous agent concentration in a range comprising any combination of the aforementioned concentrations and upper and lower limits thereof.

The water content of the pesticidal composition may vary greatly, depending on the size of the surface to be treated the degree of saturation required, the level of dilution desired or required and the size of tanks available. The composition is conveniently made up by diluting a concentrate which may be substantially water-free or which may already comprise some water.

The water content of the pesticidal concentrate may be in the range of from about 0% v/v to about 80% v/v, such as from 0% v/v to about 70% v/v, from about 0% v/v to about 65% v/v, from about 0% v/v to about 60% v/v, from about 0% v/v to about 55% v/v, from about 0% v/v to about 50% v/v, from about 0% v/v to about 45% v/v, from about 0% v/v to about 40% v/v, from about 0% v/v to about 35% v/v, from about 0% v/v to about 30% v/v, from about 15.0% v/v to about 25% v/v, from about 0% v/v to about 20% v/v, from about 0% v/v to about 15% v/v, from about 0% v/v to about 10% v/v, from about 5% v/v to about 70% v/v, from about 10% v/v to about 70% v/v, from about 15% v/v to about 70% v/v, from about 20% v/v to about 70% v/v, from about 25% v/v to about 70% v/v, from about 30% v/v to about 70% v/v, from about 35% v/v to about 70% v/v, from about 40% v/v to about 70% v/v, from about 45% v/v to about 70% v/v, from about 45% v/v to about 70% v/v, from about 45% v/v to about 70% v/v, from about 50% v/v to about 70% v/v, from about 55% v/v to about 70% v/v, from about 65% v/v to about 70% v/v, about 0% v/v, about 5% v/v, about 10% v/v, about 15% v/v, about 20% v/v, about 25% v/v, about 30% v/v, about 35% v/v, about 40% v/v, about 45% v/v, about 50% v/v, about 55% v/v, about 60% v/v, about 65% v/v, about 70% v/v, or water content in a range comprising any combination of the aforementioned contents and upper and lower limits thereof.

According to one embodiment of the invention, the pesticidal concentrate comprises from about 40% v/v to about 70% v/v water. In one specific embodiment, the pesticidal concentrate comprises about 50% v/v water.

According to one specific embodiment of the invention, the pesticidal concentrate for use in the methods of the present invention comprises:
(a) from about 5% w/v to about 25% w/v of at least one wetting agent;
(b) from about 10% v/v to about 40% v/v of at least one $C_1$ to $C_5$ alcohol;
(c) from about 0.25% w/v to about 14% w/v of at least one terpenoid; and
(d) water to volume.

Examples of suitable pesticidal compositions for uses in methods of the present invention, and methods for their preparation are also described in international patent publication No. WO 1996/028033, which is hereby incorporated by cross-reference.

The compositions or concentrates of the invention may be prepared by any suitable method known in the art. With certain components, however, solubility problems may arise. For example, where a wetting agent, ethanol, eucalyptus oil, tea tree oil and water are included in the composition, miscibility problems may arise and, under those circumstances, the composition may advantageously be prepared by firstly diluting the wetting agent with the required amount of water and to then adding sequence the alcohol, the eucalyptus oil and finally the tea tree oil, and then to mix the components to a homogenous solution.

The pesticidal composition for use in the methods of the present invention may be a dilution of a pesticidal concentrate as described above or may be made up at the desired concentration directly. The rate at which the composition is applied will clearly depend on the wetting agent(s), terpenoid(s) and alcohol(s) used. However, as a guide, a concentrate as described above may be diluted with water at a rate of from about 1:5 to about 1:100 or at any rate or range of rates therebetween, and from about 250 mL to about 10 L of the diluted concentrate may be applied per $m^2$ of the surface(s) being treated, or any volume or range of volumes therefore.

The pesticidal composition may be applied to the surface(s) of the agricultural structure of any appropriate rate which provides effective control of the one or more pests and/or one or more pathogenic organisms. However, as a guide, which is not intended to be limiting to the invention, the composition may be applied at a rate sufficient to deliver to at least the ground surface of the agricultural structure from about 0.5 g to about 70 g per $m^2$ of at least one wetting agent and form about 0.5 g to about 50 g per $m^2$ of at least one terpenoid.

Thus, according to some embodiments of the invention, the composition may be applied at a rate sufficient to deliver at least one wetting agent to at least the ground surface of the agricultural structure at a rate of from about $0.5 \text{ g·m}^{-2}$ to about $50 \text{ g·m}^{-2}$, such as from about $0.5 \text{ g·m}^{-2}$ to about $40 \text{ g·m}^{-2}$, from about $0.5 \text{ g·m}^{-2}$ to about $30 \text{ g·m}^{-2}$, from about $0.5 \text{ g·m}^{-2}$ to about $20 \text{ g·m}^{-2}$, from about $0.5 \text{ g·m}^{-2}$ to about $15 \text{ g·m}^{-2}$, from about $0.5 \text{ g·m}^{-2}$ to about $10 \text{ g·m}^{-2}$, from about $0.5 \text{ g·m}^{-2}$ to about $8 \text{ g·m}^{-2}$, from about $0.5 \text{ g·m}^{-2}$ to about $7 \text{ g·m}^{-2}$, from about $0.5 \text{ g·m}^{-2}$ to about $6 \text{ g·m}^{-2}$, from about $0.5 \text{ g·m}^{-2}$ to about $5 \text{ g·m}^{-2}$, from about $0.5 \text{ g·m}^{-2}$ to about $4 \text{ g·m}^{-2}$, from about $0.5 \text{ g·m}^{-2}$ to about $3 \text{ g·m}^{-2}$, from about $0.5 \text{ g·m}^{-2}$ to about $2 \text{ g·m}^{-2}$, from about $0.5 \text{ g·m}^{-2}$ to about $1 \text{ g·m}^{-2}$, from about $1 \text{ g·m}^{-2}$ to about $40 \text{ g·m}^{-2}$, from about $2 \text{ g·m}^{-2}$ to about $40 \text{ g·m}^{-2}$, from about $3 \text{ g·m}^{-2}$ to about $40 \text{ g·m}^{-2}$, from about $4 \text{ g·m}^{-2}$ to about $40 \text{ g·m}^{-2}$, from about $5 \text{ g·m}^{-2}$ to about $40 \text{ g·m}^{-2}$, from about $6 \text{ g·m}^{-2}$ to about $40 \text{ g·m}^{-2}$, from about $7 \text{ g·m}^{-2}$ to about $40 \text{ g·m}^{-2}$, from about $8 \text{ g·m}^{-2}$ to about $40 \text{ g·m}^{-2}$, from about $9 \text{ g·m}^{-2}$ to about $40 \text{ g·m}^{-2}$, from about $10 \text{ g·m}^{-2}$ to about $40 \text{ g·m}^{-2}$, from about $15 \text{ g·m}^{-2}$ to about $40 \text{ g·m}^{-2}$, from about $20 \text{ g·m}^{-2}$ to about $40 \text{ g·m}^{-2}$, from about $30 \text{ g·m}^{-2}$ to about $40 \text{ g·m}^{-2}$, about $1 \text{ g per m}^2$, about $2 \text{ g·m}^{-2}$, about $3 \text{ g·m}^{-2}$, about $4 \text{ g·m}^{-2}$, about $5 \text{ g·m}^{-2}$, about $6 \text{ g·m}^{-2}$, about $7 \text{ g·m}^{-2}$, about $8 \text{ g·m}^{-2}$, about $9 \text{ g·m}^{-2}$, about $10 \text{ g·m}^{-2}$, about $15 \text{ g·m}^{-2}$, about $20 \text{ g·m}^{-2}$, or an amount of wetting agent(s) in a range comprising any combination of the aforementioned amounts and upper and lower limits thereof.

According to some embodiments of the invention, the composition may be applied at a rate sufficient to deliver at least one terpenoid, essential oil or plant extract to at least the ground surface of the agricultural structure $0.2 \text{ g·m}^{-2}$ to about $30 \text{ g·m}^{-2}$, from about $0.2 \text{ g·m}^{-2}$ to about $20 \text{ g·m}^{-2}$, from about $0.2 \text{ g·m}^{-2}$ to about $15 \text{ g·m}^{-2}$, from about $0.2 \text{ g·m}^{-2}$ to about $10 \text{ g·m}^{-2}$, from about $0.2 \text{ g·m}^{-2}$ to about $7.5 \text{ g·m}^{-2}$, from about $0.2 \text{ g·m}^{-2}$ to about $5 \text{ g·m}^{-2}$, from about $0.2 \text{ g·m}^{-2}$ to about $4 \text{ g·m}^{-2}$, from about $0.2 \text{ g·m}^{-2}$ to about $3 \text{ g·m}^{-2}$, from about $0.2 \text{ g·m}^{-2}$ to about $2.5 \text{ g·m}^{-2}$, from about $0.2 \text{ g·m}^{-2}$ to about $2$ g·m$^{-2}$, from about 0.2 g·m$^{-2}$ to about 1.5 g·m$^{-2}$, from about 0.2 g·m$^{-2}$ to about 1 g·m$^{-2}$, from about 0.2 g·m$^{-2}$ to about 0.5 g·m$^{-2}$, from about 0.25 g·m$^{-2}$ to about 30 g·m$^{-2}$, from about 0.5 g·m$^{-2}$ to about 30 g·m$^{-2}$, from about 0.75 g·m$^{-2}$ to about 30 g·m$^{-2}$, from about 1 g·m$^{-2}$ to about 30 g·m$^{-2}$, from about 1.25 g·m$^{-2}$ to about 30 g·m$^{-2}$, from about 1.5 g·m$^{-2}$ to about 30 g·m$^{-2}$, from about 1.75 g·m$^{-2}$ to about 30 g·m$^{-2}$, from about 2 g·m$^{-2}$ to about 30 g·m$^{-2}$, from about 2.5 g·m$^{-2}$ to about 30 g·m$^{-2}$, from about 3 g·m$^{-2}$ to about 30 g·m$^{-2}$, from about 4 g·m$^{-2}$ to about 30 g·m$^{-2}$, from about 5 g·m$^{-2}$ to about 30 g·m$^{-2}$, from about 10 g·m$^{-2}$ to about 30 g·m$^{-2}$, about 0.5 g per m$^2$, about 0.75 g·m$^{-2}$, about 1 g·m$^{-2}$, about 1.25 g·m$^{-2}$, about 1.5 g·m$^{-2}$, about 1.75 g·m$^{-2}$, about 2 g·m$^{-2}$, about 3 g·m$^{-2}$, about 4 g·m$^{-2}$, about 5 g·m$^{-2}$, about 10 g·m$^{-2}$, or an amount of terpenoid(s) in a range comprising any combination of the aforementioned amounts and upper and lower limits thereof.

If the pesticidal compositions comprises at least one alcohol, in some embodiments the composition may be applied at a rate sufficient to deliver at least one alcohol to at least the ground surface of the agricultural structure at a rate of from about 0.5 mL·m$^{-2}$ to about 80 mL·m$^{-2}$, such as from 1 mL·m$^{-2}$ to about 70 mL·m$^{-2}$, from about 1 mL·m$^{-2}$ to about 60 mL·m$^{-2}$, from about 1 mL·m$^{-2}$ to about 50 mL·m$^{-2}$, from about 1 mL·m$^{-2}$ to about 4 mL·m$^{-2}$, from about 1 mL·m$^{-2}$ to about 30 mL·m$^{-2}$, from about 1 mL·m$^{-2}$ to about 20 mL·m$^{-2}$, from about 1 mL·m$^{-2}$ to about 15 mL·m$^{-2}$, from about 1 mL·m$^{-2}$ to about 10 mL·m$^{-2}$, from about 1 mL·m$^{-2}$ to about 5 mL·m$^{-2}$, from about 2 mL·m$^{-2}$ to about 60 mL·m$^{-2}$, from about 3 mL·m$^{-2}$ to about 60 mL·m$^{-2}$, from about 5 mL·m$^{-2}$ to about 60 mL·m$^{-2}$, from about 7.5 mL·m$^{-2}$ to about 60 mL·m$^{-2}$, from about 10 mL·m$^{-2}$ to about 60 mL·m$^{-2}$, from about 15 mL·m$^{-2}$ to about 60 mL·m$^{-2}$, from about 20 mL·m$^{-2}$ to about 60 mL·m$^{-2}$, from about 30 mL·m$^{-2}$ to about 60 mL·m$^{-2}$, from about 40 mL·m$^{-2}$ to about 60 mL·m$^{-2}$, from about 50 mL·m$^{-2}$ to about 60 mL·m$^{-2}$, about 2.5 mL·m$^{-2}$, about 5 mL·m$^{-2}$, about 7.5 mL·m$^{-2}$, about 1 mL·m$^{-2}$, about 15 mL·m$^{-2}$, about 20 mL·m$^{-2}$, about 25 mL·m$^{-2}$, about 30 mL·m$^{-2}$, or an amount of alcohol in a range comprising any combination of the aforementioned amounts and upper and lower limits thereof.

If the pesticidal composition comprises at least one nitrogenous agent, in some embodiments the composition may be applied at a rate sufficient to deliver at least one nitrogenous agent to at least the ground surface of the agricultural structure at a rate of from about 0.1 g·m$^{-2}$ to about 10 g·m$^{-2}$, from about 0.2 g·m$^{-2}$ to about 9 g·m$^{-2}$, from about 0.2 g·m$^{-2}$ to about 8 g·m$^{-2}$, from about 0.2 g·m$^{-2}$ to about 7 g·m$^{-2}$, from about 0.2 g·m$^{-2}$ to about 6 g·m$^{-2}$, from about 0.2 g·m$^{-2}$ to about 5 g·m$^{-2}$, from about 0.2 g·m$^{-2}$ to about 4 g·m$^{-2}$, from about 0.2 g·m$^{-2}$ to about 3 g·m$^{-2}$, from about 0.2 g·m$^{-2}$ to about 2 g·m$^{-2}$, from about 0.2 g·m$^{-2}$ to about 1 g·m$^{-2}$, from about 0.2 g·m$^{-2}$ to about 0.75 g·m$^{-2}$, from about 0.2 g·m$^{-2}$ to about 0.5 g·m$^{-2}$, from about 0.2 g·m$^{-2}$ to about 0.4 g·m$^{-2}$, from about 0.2 g·m$^{-2}$ to about 0.3 g·m$^{-2}$, from about 0.25 g·m$^{-2}$ to about 10 g·m$^{-2}$ from about 0.5 g·m$^{-2}$ to about 10 g·m$^{-2}$, from about 0.75 g·m$^{-2}$ to about 10 g·m$^{-2}$ from about 1 g·m$^{-2}$ to about 10 g·m$^{-2}$, from about 1.25 g·m$^{-2}$ to about 10 g·m$^{-2}$ from about 1.5 g·m$^{-2}$ to about 10 g·m$^{-2}$, from about 1.75 g·m$^{-2}$ to about 10 g·m$^{-2}$ from about 2 g·m$^{-2}$ to about 10 g·m$^{-2}$, from about 2.5 g·m$^{-2}$ to about 10 g·m$^{-2}$ from about 3 g·m$^{-2}$ to about 10 g·m$^{-2}$, from about 4 g·m$^{-2}$ to about 10 g·m$^{-2}$, from about 5 g·m$^{-2}$ to about 10 g·m$^{-2}$, from about 7.5 g·m$^{-2}$ to about 10 g·m$^{-2}$, about 0.5 g per m$^2$, about 0.75 g·m$^{-2}$, about 1 g·m$^{-2}$, about 1.25 g·m$^{-2}$, about 1.5 g·m$^{-2}$, about 1.75 g·m$^{-2}$, about 2 g·m$^{-2}$, about 3 g·m$^{-2}$, about 4 g·m$^{-2}$, about 5 g·m$^{-2}$, about 10 g·m$^{-2}$, or an amount of nitrogenous agent(s) in a range comprising any combination of the aforementioned amounts and upper and lower limited thereof.

According to one specific embodiment of the invention, the pesticidal composition is applied at a rate sufficient to deliver to each m$^2$ of at least the ground surface of the agricultural structure:

(a) from about 1 g to about 20 g of at least one wetting agent; and (b) from about 0.1 g to about 10 g of at least one terpenoid.

According to another specific embodiment of the invention, the pesticidal composition is applied at a rate sufficient to deliver to each m$^2$ of at least the ground surface of the agricultural structure:

(a) from about 1 g to about 20 g of at least one wetting agent;

(b) from about 2 mL to about 40 mL of at least one $C_1$ to $C_5$ alcohol;

(c) from about 0.1 g to about 10 g of at least one terpenoid; and (d) from about 0.1 to about 10 g of at least one nitrogenous agent.

According to another specific embodiment of the invention, the pesticidal composition is applied at a rate sufficient to deliver to each m$^2$ of at least the ground surface of the agricultural structure:

(a) from about 1 g to about 20 g of at least one wetting agent selected from α-olefin sulphonates, an alkali or alkaline earth metal salt of an alkyl or aralkyl sulphuric or sulphonic acid ester, coconut diethylamide or any combination there;

(b) from about 2 mL to about 40 mL of at least one $C_2$ to $C_5$ alcohol;

(c) from about 0.1 g to about 10 g of a terpenoid mixture comprising at least terpinen-4-ol and 1,8-cineole; and (d) from about 0.1 to about 10 g of urea.

According to another specific embodiment of the invention, the pesticidal composition is applied at a rate sufficient to deliver to each m$^2$ of at least the ground surface of the agricultural structure:

(a) from about 1 g to about 20 g of at least one wetting agent selected from α-olefin sulphonates, an alkali or alkaline earth metal salt of an alkyl or aralkyl sulphuric or sulphonic acid ester, or any combination thereof;

(b) from about 0.05 g to about 1 g of coconut diethylamide;

(c) from about 15 mL to about 30 mL of ethanol;

(d) from about 0.25 g to about 5 g of a mixture of tea tree and eucalyptus oils; and (e) from about 0.5 to about 5 g of urea.

The pesticidal compositions may be applied to the surface(s) of the agricultural structure by an appropriate means as known in the art, including pouring and spraying.

For example, it is possible to mix the composition with a propellant, as is well established and known in the art, in order to provide a sprayable aerosol composition. Alternatively, the composition may be applied as a spray delivered from a pressurized pump-pack. Foaming or gelling agents may be included in the composition(s), especially if non-horizontal surfaces are to be treated, to aid in prolonging contact time between the surface(s) and the composition.

As described above, the composition may also be applied to at least a ground surface of the agricultural structure as a composition comprising animal litter and/or zeolite or analogue thereof pre-charged with the composition either instead of, or as well as applying the composition to the surface(s) of the agricultural structure before introduction of the animal litter and/or zeolite or analogue thereof.

The animal litter and/or zeolite or analogue thereof may be pre-charged with the composition at any suitable rate up to saturation of the material with the composition. The rate of charging of the zeolite or analogue thereof with the pesticidal composition will depend on a number of parameters, including the absorptive/adsorptive capacity of the zeolite or analogue thereof, on the rate of application of zeolite or analogue thereof to the ground surface of the agricultural structure, and on the nature of the pesticidal composition. However, as a guide to rates of application of pesticidal composition to zeolites or analogues thereof, which is not intended to be limiting to the practice of the invention, the composition may be added to, or applied to the zeolite or analogue thereof at a rate which, when the zeolite or analogue thereof is applied to the ground surface of the agricultural structure, the composition is present in an amount that would be achieved if applied to the ground surface of the structure at a rate as described above. In an embodiment, a composition as described above comprising a wetting agent and a terpenoid, essential oil or plant extract, the composition is added to or applied to the zeolite or analogue thereof at a rate of from about 1 g wetting agent per kilogram zeolite or analogue thereof to about 200 g wetting agent per kilogram zeolite or analogue thereof, such as from about 5 g/kg to about 150 g/kg, about 5 g/kg to about 100 g/kg, about 5 g/kg to about 90 g/kg, about 5 g/kg to about 80 g/kg, about 5 g/kg to about 70 g/kg, about 5 g/kg to about 60 g/kg, about 5 g/kg to about 50 g/kg, about 5 g/kg to about 40 g/kg, about 5 g/kg to about 30 g/kg, about 5 g/kg to about 20 g/kg, about 5 g/kg to about 10 g/kg, about 10 g/kg to about 100 g/kg, about 20 g/kg to about 100 g/kg, about 30 g/kg to about 100 g/kg, about 40 g/kg to about 100 g/kg, about 50 g/kg to about 100 g/kg, about 60 g/kg to about 100 g/kg, about 70 g/kg to about 100 g/kg, about 80 g/kg to about 100 g/kg, about 90 g/kg to about 100 g/kg, about 10 g/kg to about 2 g/kg, about 30 g/kg to about 40 g/kg, about 50 g/kg to about 60 g/kg, about 70 g/kg, about 80 g/kg, about 90 g/kg, about 100 g/kg, about 125 g/kg, about 150 g/kg, about 175 g/kg, or about 200 g/kg, or an amount of composition in a range comprising any combination of the aforementioned amounts and upper and lower limits thereof.

Pests and Pathogenic Organisms Targeted by Methods of the Present Invention

Compositions as described above have been shown to exhibit pesticidal and repellent properties in relation to a broad range of organisms. In particular the composition has been shown to be especially active for killing and repelling beetles (and larvae thereof), cockroaches, ants, flies, mosquitoes, spiders, silver fish, moths as well as numerous other insect species.

Pests particularly targeted by the methods of the present invention include insects. According to an embodiment, the insect is a beetle or larva thereof, this group of insects including a number of major pests of agricultural structures and, in particular, grain storage structures and animal rearing enclosures. According to an embodiment the beetle is a member of the Anobiidae, Anthribidae, Bostrichidae (especially *Rhizopertha dominica*—lesser grain borer), Chrysomelidae, Curculionidae, Dermestidae, Laemophloeidae, Nitidulidae, Scarabaeidae, or Tenebrionidae. One family of beetles particularly targeted by the methods of the present invention is the tenbrionid family, which includes the genuses *Alphitobius, Gnathocerus, Latheticus, Omophlus, Tenebrio*, or *Tribolium*, which include major agricultural pests, including the darkling beetle, *Alphitobius diaperinus* (or lesser mealworm), *Tenbrio molitor* (yellow mealworm), *Tribolium confusum* (confused flour beetle) and *Tribolium castaneum* (rust-red flour beetle).

The compositions as described above may also be disinfectant and active against one or more pathogenic organisms selected from viruses, bacteria, fungi, protozoans, helminthes or cestodes directly and/or indirectly by being active against vectors responsible for carrying them, including a number of pests described above, including the darkling beetle. The pathogenic organisms which may be controlled, directly or indirectly, by methods of the present invention include viruses, bacteria, fungi, protozoans and helminthes.

The darkling beetle is known as a vector for: viral diseases including leucosis or Marek's disease, Gumboro disease, turkey coronavirus, Newcastle disease, infectious bursal disease, reovirus, enterovirus, fowl pox and avian influenza; bacterial pathogens including bacteria of the genus *Salmonella, Campylobacter, Escherichia*, and *Staphylococcus*; fungal pathogens, including fungi of the genus *Aspergillus*; and can act as intermediate hosts for caecal nematodes, tapeworms and protozoa, including protozoa of the genus *imeria* associated with coccidiosis.

According to an embodiment, the compositions for use in the methods of the present invention are also toxic and/or repellent to mosquitoes and/or flies.

Maintenance and Disinfestation Procedures for Animal Enclosures

The methods described above find particular application as maintenance, disinfestation or maintenance and disinfestation methods for controlling at least one pest insect species in intensively farmed animal enclosures. As described above, a pesticidal composition (which does not comprise an organophosphate or carbamate pesticide other than low toxicity growth regulators, such as fenoxycarb) as described above may be applied to at least the ground surface of the animal enclosure, although it is advantageously also applied to the walls of the enclosure, as pests and/or pathogens may also reside in the walls. Fresh litter is then applied to the treated ground surface of the enclosure before re-introduction of animals to the enclosure. A layer of zeolite or analogue thereof may be applied to the ground surface of the enclosure before fresh litter is introduced, providing at least the advantage of providing an absorbent or adsorbent for nitrogenous wastes from the animals. The zeolite or analogue thereof may provide the advantages of reducing the incidence of potentially toxic or even deadly ammonia flushes (by binding ammonium ions) and deodorizing the enclosures and resulting waste litter.

As an alternative, or additional to treating the ground surface with the pesticidal composition, and as described above, the pesticidal composition may be applied to animal litter and/or zeolite or analogue thereof, before or after the litter and/or zeolite or analogue thereof is applied to the ground surface of the enclosure. This provides the advantage of providing a barrier to pests, and associated diseases, entering the animal enclosure from sites within the ground surface.

In particular the embodiment the method comprises:
applying a pesticidal composition to at least the ground surface of the enclosure, wherein the composition does not comprise an organophosphate or a carbamate pesticide;
applying a layer of zeolite or analogue thereof to the treated ground surface and
Advantageously the composition is applied to the walls of the enclosure, as well as to the ground surface, to replace the currently used alkaline wash.

As described earlier, advantageously the pesticidal composition may also be applied to the zeolite of analogue thereof either before or after it is applied to the ground surface of the animal enclosure.

The pesticidal composition may be applied at any suitable rate as described above. According to one embodiment, the composition is applied at a rate sufficient to deliver to each m² of at least the ground surface of the agricultural structure:

(a) from about 1 g to about 20 g of at least one wetting agent;
(b) from about 2 mL to about 40 mL of at least one $C_1$ to $C_5$ alcohol; and
(c) from about 0.1 g to about 10 g of at least one terpenoid.

According to a more specific embodiment of the invention, the pesticidal composition is applied at a rate sufficient to deliver to each m² of at least the ground surface of the agricultural structure:

(a) from about 1 g to about 20 g of at least one wetting agent;
(b) from about 2 mL to about 40 mL of at least one $C_1$ to $C_5$ alcohol;
(c) from about 0.1 g to about 10 g of at least one terpenoid; and
(d) from about 0.1 to about 10 g of at least one nitrogenous agent.

According to another specific embodiment of the invention, the pesticidal composition is applied at a rate sufficient to deliver to each m² of at least the ground surface of the agricultural structure:

(a) from about 1 g to about 20 g of at least one wetting agent selected from α-olefin sulphonates, an alkali or alkaline earth metal salt of an alkyl or aralkyl sulphuric or sulphonic acid ester, coconut diethylamide or any combination thereof;
(b) from about 2 mL to about 40 mL of at least one $C_2$ to $C_5$ alcohol;
(c) from about 0.1 g to about 10 g of a terpenoid mixture comprising at least terpinen-4-ol and 1,8-cineole; and
(d) from about 0.1 to about 10 g of urea.

According to another specific embodiment of the invention, the pesticidal composition is applied at a rate sufficient to deliver to each m² of at least the ground surface of the agricultural structure:

(a) from about 1 g to about 20 g of at least one wetting agent selected from α-olefin sulphonates, an alkali or alkaline earth method salt of an alkyl or aralkyl sulphuric or sulphonic acid ester, or any combination thereof;
(b) from about 0.05 g to about 1 g of coconut diethylamide;
(c) from about 15 mL to about 30 mL of ethanol;
(d) from about 0.25 g to about 5 g of a mixture of tea tree and eucalyptus oils; and
(e) from about 0.5 to about 5 g of urea.

The one particular embodiment, the pesticidal composition for use in such maintenance/disinfestation methods as described above may comprise a dilution of a concentrate comprising:

(a) from about 5% w/v to about 25% w/v of at least one wetting agent;
(b) from 10% v/v to about 40% v/v of at least one $C_1$ to $C_5$ alcohol;
(c) from 0.25% w/v to about 14% w/v of at least one terpenoid; and
(d) water;

wherein said dilution is dilution with water at a rate of from about 1 part concentrate to 10 parts water to about 1 part concentrate to about 60 parts water.

Such a composition may be applied to the surface(s) of the animal enclosure at a rate of from about 250 mL/m² to about 10 L/m². According to an embodiment, the composition is a 1:20 dilution of a composition as described immediately above, and is applied to the surface(s) of the structure at a rate of from about 500 mL/m² to about 3 L/m².

The terpenoids may be selected from those described above, and may be monoterpenes. According to a specific embodiment, the terpenoids comprise 1,8-cineole, terpen-4-ol, terpinen-4-ol, or any combination thereof.

The pesticidal composition may comprise a 1:5 to a 1:100 dilution of a concentrate comprising from about 10% w/v to about 15% w/v of α-olefin sulphonated, sodium lauryl sulphate, sodium dodecylbenzene sulphonated or a combination thereof, from about 25% v/v to about 35% v/v of ethanol and from about 2% w/v to about 14% w/v combined of tea tree oil and eucalyptus oil.

According to an embodiment of the maintenance/disinfestation methods as described above, the at least one insect species to be controlled comprises a beetle or larva thereof. In a specific embodiment the insect species is *Alphitobius diaperinus*, which is also a known vector or carrier of a number of pathogenic organisms associated with diseases of poultry, as described above. The compositions as described above are active against the beetle, and may be active against one or more of the pathogenic organisms and therefore control those pathogens either directly or indirectly. Thus, according to an embodiment, the methods of the invention are for the control of at least the darkling beetle and its larve (*Alphitobius diaperinus*; lesser mealworm), as well as any associated pathogenic organisms in poultry sheds.

Fertilizers and Soil Improvement/Remediation Agents

Waste litter obtained from animal enclosures treated by methods of the present invention may be processed into fertilizer produces, as they are rich in nitrogenous waste from the animals. the waste litter from enclosures in which a layer of zeolite or analogue thereof provide the added advantage of being able to be processed into a fertilizer product with at least partial slow or controlled release of nutrients due to the ion exchange capacity of the zeolite or analogue thereof, which may result in binding of ammonium and slow release thereof afterwards and which will also improve the soil it is applied to by increasing the soils ion exchange capacity. The zeolite or analogue thereof may also aide in deodorizing the litter (during or after use in the animal enclosures) providing for a less offensive fertilizer product (which is particularly desirable for urban situations—existing poultry-shed litter based fertilizers are strongly and unpleasantly odoured), which deodorizing may also be aided by use of a pesticidal composition comprising terpenoids.

Zeolite containing waster litter may also be processed into a soil improvement product, not only due to its at least partial slow/controlled nutrient release properties, but also due to its ion exchange capacity which may increase the soil ion exchange capacity and provide buffering power, which may be important for acidified soils, including acid sulphate soils (which has very low pH values at which most plant, animal and microbial life may not grow).

A fertilizer or soil improvement product may be manufactured from waste litter by any method known in the art. In one embodiment the waste litter may be ground or comminuted and then pelletized, optionally being sterilized during the process. The waste litter may also be passed through an extruder or pelletizer, which grind/comminution optionally being carried out first. The waste litter may also be mixed, and optionally ground/comminuted prior to direct application to a soil. Other ingredients, such as water, one or more alkali or buffering agents (such as lime or gypsum) and/or one or more deodorants may also be added to the waste litter before or during preparation of the fertilizer or soil improvement product.

In a particular embodiment, a soil improvement product as described above may be added/incorporated into an acid sulphate soil to raise the pH to a controlled pH 5.5 to 8.0 range, to control leaching and run off of environmental contaminants, and to improve and rejuvenate the soil for regrowth.

The fertilizer or soil improvement product may be applied to the soil by any appropriate method known in the art, including direct application to the surface of a soil, optionally then cultivating or hoeing the soil, direct drilling or deep-ripping the product into the soil, or by more manual means, including use of shovels, mattocks, hoes and similar.

Preferred forms of the present invention will now be described, by way of example only, with reference to the following examples, including comparative data, and which are not to be taken to be limiting to the scope or sprit of the invention in any way.

EXAMPLES

Example 1

Formulation of Preferred Disinfectant/Insecticide Composition

A concentrate of the composition was prepared with the following components/concentrations, and then diluted as required/desired:
12.5% wetting agent comprising α-olefin sulphonated (approximately 72% w/w) and sodium dodecylbenzene sulphonated (approximately 28% w/w).
1% w/v coconut diethylamide
3% v/v tea tree oil
2% v/v eucalyptus oil
26.5% ethanol
5% w/v urea
50% water The composition was prepared by firstly diluting the wetting agent and coconut diethylamide with the required amount of water, then adding the sequence the alcohol, the eucalyptus oil, the tea tree oil, then the remaining ingredients. The components were then mixed to a homogenous solution.

Example 2

Maintenance/Disinfestation of Chicken Sheds
Control method

1. Previous batch of chickens were removed from the shed and taken to the processing plant.
2. All chicken floor litter was removed from the shed.
3. The shed was then washed down using an alkaline detergent.
4. Prolong® (composition comprising 100 g/kg cyfluthrin, a pyrethroid) treatment—insecticide (5 kg diluted into 250 L water) was sprayed on all surfaces of the shed.
5. The shed was then disinfected by spraying Prolong® (15% w/v solution of glutaraldehyde: 8 L diluted in 400 L water) on all surfaces of the shed. Formalin (21.5 L in 4,300 L water) can be used instead of, or as well as the Prolong® treatment.
6. Fresh litter was laid, and the shed reloaded with poultry for a growing period of 45-50 days.
7. Market-ready chickens harvested, weight gain and yield determined and beetle (and larvae) infestation determined.

Experimental Method

The procedure was similar to that for the control method, although steps 3 to 5 were carried out using a pesticidal concentrate manufactured according to the formulation provided in Example 1, and diluted 1:33 or 1:66 with water to form the working pesticidal composition before application to the walls and ground surface of a chicken shed. 2,000 L of each composition was applied to the whole shed, with approximately 75% being sprayed on the ground surface of each shed (approximately 1,500 m$^2$) and the remainder on the shed walls and ceiling.

Relative to the control chicken shed, the treated sheds showed 70% and 32% reductions in beetle and larvae numbers (1:30 1:60 dilutions respectively). Chicken yields (weight of chicken per kilogram of feed) were also increased.

It will be appreciated that, although a specific embodiment of the invention has been described herein for the purpose of illustration; various modifications may be made without deviating from the spirit and scope of the invention as defined in the following claims.

The invention claimed is:
1. A method for controlling one or more pests or pathogenic organisms or a combination thereof in an agricultural structure consisting essentially of applying a composition consisting essentially of effective amounts of coconut diethylamide, tea tree oil, eucalyptus oil, ethanol, and urea to a surface of the structure susceptible to infestation or colonization by said pests or pathogenic organisms.

* * * * *